(12) United States Patent
Menon et al.

(10) Patent No.: US 8,142,723 B2
(45) Date of Patent: *Mar. 27, 2012

(54) TAG FREE BIO SENSING MICRO STRIP

(75) Inventors: Naresh Menon, Pasadena, CA (US); John D. Minelly, Bothell, WA (US)

(73) Assignee: Chromologic, LLC, Pasadena, CA (US)

( * ) Notice: Subject to any disclaimer, the term of this patent is extended or adjusted under 35 U.S.C. 154(b) by 938 days.

This patent is subject to a terminal disclaimer.

(21) Appl. No.: 12/098,737

(22) Filed: Apr. 7, 2008

(65) Prior Publication Data

US 2011/0046021 A1 Feb. 24, 2011

Related U.S. Application Data

(63) Continuation-in-part of application No. 11/120,030, filed on May 2, 2005, now Pat. No. 7,354,772.

(60) Provisional application No. 60/568,795, filed on May 7, 2004, provisional application No. 60/567,195, filed on May 3, 2004.

(51) Int. Cl.
*G01N 21/00* (2006.01)
*H01L 31/00* (2006.01)
*G01B 9/02* (2006.01)

(52) U.S. Cl. .................. 422/82.05; 250/214.1; 356/519

(58) Field of Classification Search ............... 422/82.05; 250/214.1; 356/519
See application file for complete search history.

(56) References Cited

U.S. PATENT DOCUMENTS

| | | | |
|---|---|---|---|
| 5,216,237 A | 6/1993 | Ritchie et al. | |
| 5,229,833 A | 7/1993 | Stewart | |
| 5,440,417 A | 8/1995 | Chung et al. | |
| 5,502,563 A | 3/1996 | Dunn et al. | |
| 5,513,205 A | 4/1996 | Rubinstein | |
| 5,538,850 A | 7/1996 | King et al. | |
| 5,608,519 A | 3/1997 | Gourley et al. | |

(Continued)

FOREIGN PATENT DOCUMENTS

SU 1819081 A1 5/1995

(Continued)

OTHER PUBLICATIONS

Vollmer, et al., "Protein detection by optical shift of a resonant microcavity," Applied Physics Letters, vol. 80, No. 21, pp. 4057-4059, (May 27, 2002).

(Continued)

*Primary Examiner* — Lore Jarrett (74) *Attorney, Agent, or Firm* — Knobbe Martens Olson & Bear LLP (57) ABSTRACT

In one embodiment, a system for determining information about an assay incorporates a filter assembly that includes an optical structure configured to be removably attachable to a laser resonating cavity of the system, the optical structure being configured to form a portion of the laser resonating cavity such that it reflects light propagating through a gain medium in the laser resonating cavity when attached thereto. The optical structure can include a first surface having an array of one or more sites, each site containing an assay, and a second surface configured such that the second surface is disposed within the laser resonating cavity forming a portion of the laser resonating cavity. The optical structure is configured to optically interact with the assay to change one or more characteristics of light in the laser resonating cavity based on a reaction that occurs in an assay on said first surface.

22 Claims, 7 Drawing Sheets

U.S. PATENT DOCUMENTS

| | | | |
|---|---|---|---|
| 5,793,485 | A | 8/1998 | Gourley |
| 5,905,571 | A | 5/1999 | Butler et al. |
| 6,097,741 | A | 8/2000 | Lin et al. |
| 6,115,401 | A | 9/2000 | Scobey et al. |
| 6,264,328 | B1 | 7/2001 | Williams et al. |
| 6,287,871 | B1 | 9/2001 | Herron et al. |
| 6,332,363 | B1 * | 12/2001 | Molloy et al. ............ 73/776 |
| 6,606,331 | B2 | 8/2003 | Sousa et al. |
| 6,678,288 | B2 | 1/2004 | Rice |
| 6,771,993 | B2 | 8/2004 | Rule et al. |
| 7,057,720 | B2 | 6/2006 | Caracci et al. |
| 7,354,772 | B2 * | 4/2008 | Menon et al. ............ 436/164 |
| 2003/0081309 | A1 | 5/2003 | Nishi et al. |
| 2004/0223881 | A1 | 11/2004 | Cunningham et al. |
| 2004/0235062 | A1 | 11/2004 | Nakajima et al. |
| 2005/0094158 | A1 | 5/2005 | Paldus et al. |

FOREIGN PATENT DOCUMENTS

WO    WO 2004102170 A1    11/2004

OTHER PUBLICATIONS

Pearson, et al., "Analytical aspects of biosensors," Ann. Clin. Biochem., vol. 37, pp. 119-145, (2000).

* cited by examiner

TAG FREE BIO SENSING MICRO STRIP

RELATED APPLICATIONS

This application is a continuation-in-part of U.S. application Ser. No. 11/120,030, filed May 2, 2005, now U.S. Pat. No. 7,354,772, which claims the benefit of U.S. Provisional Application No. 60/568,795 filed May 7, 2004, and U.S. Provisional Application No. 60/567,195 filed May 3, 2004, all of which are incorporated by reference in their entireties.

BACKGROUND OF THE INVENTION

1. Field

The field of the invention relates to laser analyte detection systems and methods.

2. Description of the Related Technology

Microarray assays can be used to determine the presence of an analyte or compare genetic expression between two or more sample groups on thousands of genes per experiment. Typically, labels (e.g., secondary identifier tag) are used to detect the bio-molecular interactions, usually employing luminescent detection principles such as fluorescence, bioluminescence, or chemiluminescence, to detect the presence of specific chemical species. The array results are useful in molecular disease classification, gene and pathway discovery, tumor prognosis and sub-classification, drug development, and the prediction of response to treatment. However, such experiments have suffered from multiple problems including artifacts in sample preparation and labeling, software definition of each spot or feature, determination of signal level, and reproducibility of signals within a single array or across arrays. For example, experimental variations within a tissue source or type are often larger than the distinguishing differences, e.g., between cancerous and non-cancerous expressions.

Laser-based systems used for analyte detection may also require labels to detect bio-molecular interactions and require direct exposure of the sample to a laser beam, which can complicate the detection process. Accordingly, there is a need to develop an alternative method for gene expression measurements that overcomes the above-described and other problems in the art.

SUMMARY OF CERTAIN INVENTIVE ASPECTS

The system, method, and devices of the invention each have several aspects, no single one of which is solely responsible for its desirable attributes. Without limiting the scope of this invention as expressed by the claims which follow, its more prominent features will now be discussed briefly. After considering this discussion, and particularly after reading the section entitled "Detailed Description of Certain Embodiments," one will understand how the features of this invention provide advantages that include, in a first embodiment, a method of determining information about an assay, including positioning a filter assembly, having an assay disposed on its surface, relative to a light source such that light from the light source is incident on the filter assembly and at least a portion of the light incident on the filter assembly is reflected from the filter assembly, illuminating the filter assembly with light from the light source, receiving light reflected from the filter assembly in an optical element, analyzing one or more characteristics of the light received in the optical element to determine information about a reaction in the assay, where a reaction in the assay results in a change of one or more characteristics of the light received from the filter assembly.

In one aspect of the first embodiment, the light source comprises a laser light source. In another aspect of the first embodiment the characteristic of the light that is analyzed is wavelength. In another aspect, the method further includes disposing the assay on the filter assembly, and exposing the assay to one or more reagents. In another aspect, the assay is disposed on a first surface of the filter assembly and the light from the light source is incident on a second surface of the filter assembly. In some embodiments, the method further comprises collimating the light from the light source before it is incident on the filter assembly, and collimating the light reflected from the lens assembly before it is received in the optical element. In another aspect of the first embodiment, the reaction in the assay results in a physical change in the assay that changes the refractive index of the surface of the filter assembly on which the assay is disposed. In yet another aspect, analyzing the received light comprises analyzing one or more characteristics of the light received from the filter assembly after a physical change has occurred in the assay in relation to one or more characteristics of the light illuminating the filter assembly before the physical change occurred in the assay. The light source can include a broadband light source and a filter configured to transmit one or more wavelengths. In another aspect, the method further includes positioning the filter assembly such that the assay is disposed on the opposite side of the filter assembly as the incident light.

A second embodiment includes a method of determining information about an assay disposed on a first surface of a filter assembly, including incorporating the filter assembly in an optical resonating cavity such that the assay is disposed exterior to the resonating cavity, providing light to the filter assembly such that at least a portion of the light incident on the filter assembly is reflected by the filter assembly into the optical resonating cavity, receiving at least a portion of the light from the optical resonating cavity, and determining information about a reaction in the assay by analyzing one or more characteristics of the received light where a reaction that occurred in the assay results in a physical change in the assay that is manifested in one or more characteristics of the light in the optical cavity. In one aspect of the second embodiment, the filter assembly is configured to change the wavelength, intensity, and/or phase of light in the resonating cavity when a reaction occurs in the assay. In a second aspect, the characteristic of the light that is analyzed is its wavelength. In some configurations, the light source comprises a broadband light source and a filter configured to transmit one or more wavelengths. In other configurations, the light source comprises a laser light source.

A third embodiment includes a system for analyzing an assay, including a structure having a resonating cavity configured to receive a filter assembly having an assay disposed on an assay receiving portion of the filter assembly, such that the assay receiving portion is positioned exterior to said resonating cavity, a light source positioned to provide light to the filter assembly when the filter assembly is received by said structure such that light from the light source impinges on the filter assembly and at least a portion of the light is reflected from the filter assembly into the resonating cavity, an optical element for receiving light reflected from the filter assembly, and an analysis system connected with said optical element and configured to detect one or more characteristics of the light received by said optical element and determine information about a reaction of the assay based on the one or more detected characteristics. In one aspect, the optical element is positioned within the resonating cavity. In another aspect of the third embodiment, the system further includes the filter assembly. In another aspect, the system further includes a lens assembly for collimating light, said lens assembly positioned in said resonating cavity relative to said laser light source and said optical element such that light from the laser light source propagates through said lens assembly and light reflected from the filter assembly propagates through said lens assembly. In another aspect, the filter assembly comprises a Fabrey-Perot etalon filter.

A fourth embodiment includes a system for analyzing an assay, including a structure including a resonating cavity configured to receive a filter assembly such that an assay disposed on a surface of the filter assembly is positioned outside said resonating cavity, and an analysis system configured to receive light emitted from the resonating cavity and further configured to detect information about a reaction in the assay based on the light received from the resonating cavity where a reaction in the assay results in a change to one or more characteristics of the light in the resonating cavity. In an aspect of the fourth embodiment, the system further includes the filter assembly.

A fifth embodiment includes a filter assembly configured to form a portion of a laser resonating cavity of a system that determines information about an assay by analyzing light emitted from the laser resonating cavity, the filter assembly including an optical structure comprising one or more filters configured to receive light from a light source through a first surface and reflect at least a portion of the received light, and an assay disposed on a second surface of said optical structure, said second surface being disposed substantially parallel to and opposite said first surface where said assay is configured to optically interact with said optical structure to change an optical characteristic of the light propagating through the laser resonating cavity based on a reaction that occurs in the assay. In one aspect, the optical characteristic changed by a reaction in the assay is the wavelength. In another aspect, the assay and optical structure interact to change one or more properties of the laser resonating cavity that affects the wavelength of light emitted from the resonating cavity.

A sixth embodiment includes a system for determining information about an assay, including means for positioning a filter assembly, having an assay disposed on its surface, in a resonating cavity relative to a light source such that light from the light source is incident on the filter assembly and at least a portion of the light incident on the filter assembly is reflected from the filter assembly, means for illuminating the filter assembly with light from the light source, means for receiving light reflected from the filter assembly in an optical element, means for analyzing one or more characteristics of the light received in the optical element to determine information about a reaction in the assay, wherein a reaction in the assay results in a change of one or more characteristics of the light received from the filter assembly.

DETAILED DESCRIPTION OF CERTAIN EMBODIMENTS

The following detailed description is directed to certain specific embodiments of the invention. However, the invention can be embodied in a multitude of different ways as defined and covered by the claims. In this description, reference is made to the drawings wherein like parts are designated with like numerals throughout.

Embodiments of the invention include methods and systems for determining the presence, concentration, or amount of a substance in a fluid. Such methods and apparatus have applicability in the field of clinical analysis, but also, for example, in wet chemical analysis in general, and in gas analysis. The embodiments relate to methods and systems/devices that, as a consequence of a biochemical interaction, will alter one or more characteristics of light from a laser (e.g., optical fiber lasers). The embodiments can include a laser that changes its lasing frequency as a function of changes in its cavity parameters. The laser used for some embodiments can produce a laser beam over a large bandwidth. For example, some embodiments include a fiber laser that provides gain over a wavelength span of about 30 nanometers (nm) when the laser cavity of the fiber laser changes due to the presence of an analyte disposed such that it influences the parameters of the laser cavity. In some embodiments, the presence of an analyte in an appropriately prepared assay can be detected by analyzing the change in one or more characteristics of a laser beam, e.g., wavelength, phase, intensity, or frequency.

Figure 1:
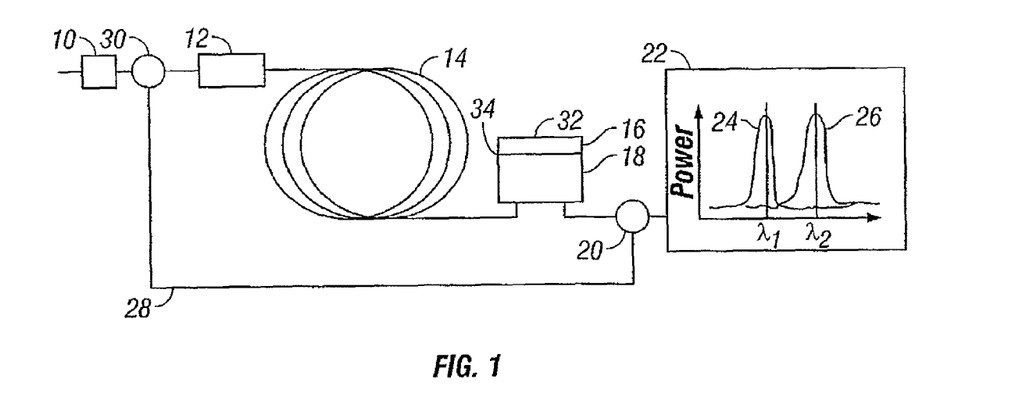
FIG. 1 is a schematic diagram illustrating one embodiment of a bio-sensor system having a sensor site for detecting an analyte without the aid of secondary identifier tags.

FIG. 1 illustrates one embodiment of the invention, comprising a system having a single sensor site for detecting an analyte without the aid of secondary identifier tags. The system includes an optical pump 10 coupled to a gain medium 14 via an optical coupler 30 and an optical isolator 12. The gain medium 14 can be an appropriately doped optical fiber, as shown in this embodiment, where the doping can be, for example, erbium, thulium or a combination thereof.

The first optical coupler 30 is disposed between the optical isolator 12 and the optical pump 10 and configured such that light from the optical pump 10 passes through the first optical coupler 30 to the optical isolator 12. The first optical coupler 30 is also coupled to one end of an optical fiber 28. The optical isolator 12 is disposed between the first optical coupler 30 and the gain medium 14 to regulate the direction of the propagation of light from the optical pump 10, through the first optical coupler 30, through the optical isolator 12 to the gain medium 14.

The gain medium 14 is connected to a sensor site 34 which includes an optical assembly 18 configured to receive and couple to a filter assembly 16. The filter assembly 16 has a biochemical assay 44 (FIG. 5) disposed on a portion of its surface 32. The combination of the filter assembly 16 and the biochemical assay 44 are referred to herein as the "sensor 34." When the filter assembly 16 is coupled to the optical assembly 18, it becomes part of a laser resonating cavity and the surface 32 having the assay is disposed exterior to the resonating cavity. When the filter assembly 16 is coupled to the optical assembly 18, the optical assembly 18 is configured to receive light from the gain medium 14, and propagate the light so that it is incident on a surface of the filter assembly 16 disposed within the resonating cavity. The presence of an analyte as detected by the assay 44 on the surface 32 changes the refractive index of the filter assembly 16, which changes one or more characteristics of the light in the resonating cavity.

In some embodiments, the filter assembly 16 can include a reflective filter, e.g., a Fabrey-Perot etalon filter. The reflective filter can have one or more layers, where each layer can have the same or different optical properties. In some embodiments, the filter assembly 16 can include a Bragg reflector. In some embodiments, the filter assembly 16 can include a Fabrey-Perot resonating cavity filter. In some embodiments, the filter assembly 16 can include a transmission filter, e.g., a fiber Fabrey-Perot etalon filter, a fiber-coupled Fabrey-Perot micro-etalon filter, or the like. The transmission filter can have one or more layers, where each layer can have the same or different optical properties. In some embodiments, the filter assembly 16 can include a reflection filter, e.g., a fiber Bragg grating filter, a set of sampled fiber Bragg gratings, a Fabrey-Perot etalon filter, or the like. By providing the filter assembly 16 with particular optical characteristics, the frequency of the fiber laser can be latched, e.g., the lasing frequency can be set or "locked" to a particular frequency value. In some embodiments, the filter assembly 16 can be a fiber coupled assembly, which can include dissimilar fiber waveguides.

A second optical coupler 20 connects the optical assembly 18 to the optical fiber 28 and also to an analyzer 22. In some embodiments, the analyzer 22 includes a spectrum analyzer. The second optical coupler 20 directs a portion of the light it receives from the optical assembly 18 to the optical fiber 28 and a portion to the analyzer 22. For example, in one embodiment the second optical coupler 20 directs about 5% of the light it receives to the analyzer 22 and about 95% to the optical fiber 28. Accordingly, a circulating loop is formed that propagates light through the optical isolator 12, the gain medium 14, the optical assembly 18, and the optical fiber 28. In this embodiment, this loop constitutes the resonating cavity. Perturbing the loss profile of the resonating cavity results in a shift in optical wavelength and power of the laser. The loss profile can be changed by replacing the optical filter assembly 16 having certain optical properties with another optical filter assembly 16 having one or more different optical properties. It will be appreciated that in some embodiments, the resonating cavity can include planar waveguide elements instead of one or more of the parts described herein. In some embodiments, a linear laser cavity is used.

The laser light in the resonating cavity will have known optical characteristics based on the optical properties of the filter assembly 16. It will be appreciated that if the optical properties of the filter assembly 16 change, the optical characteristics of the laser light can also change. The optical characteristics of the filter assembly 16 can be so designed and configured such that one or more optical characteristics of the filter assembly 16 are influenced by changes that occur to one or more of its surfaces. For example, a change occurring in a biochemical reaction site (e.g., an assay) disposed on the surface 32 of the filter assembly 16 can result in a change in the refractive index at surface 32. Changing the refractive index at a single surface, e.g., the surface 32 disposed on the outside of the optical assembly 18 in this embodiment, can affect one or more other optical characteristics of the filter assembly 16. For example, a change in the refractive index at any filter surface including any intermediate layer of the filter assembly 16 can result in a change in the wavelength dependant loss of the filter assembly 16. By detecting whether a change in the wavelength has occurred, information about a reaction in the assay can be determined.

It will be appreciated that the analyzer 22 can be configured to determine optical characteristics of the light it receives from the optical assembly 18. In some embodiments, the analyzer 22 can read the optical wavelength, and/or the shift in wavelength that results from a change in optical characteristics of the filter assembly 16. In one embodiment, the analyzer 22 can determine the shift in lasing frequency of the fiber laser by scanning for the filter position that corresponds to the maximum optical power and correlating the filter position to a wavelength value.

Still referring to FIG. 1, Graphs 24 and 26 shown in the analyzer 22 are examples of representations of the wavelength of the laser light in the resonating cavity (x-axis) verses optical power (y-axis) for the system In a first state, represented by graph 24, the system is configured with a filter assembly 16 having a first assay disposed on one of its surfaces 32 that is exterior to the optical assembly 18. The first assay is not bound to an analyte and therefore graph 24 represents a first state of the system with a first set of optical characteristics associated with the laser light. In this example, the analyzer 22 has determined the optical power of graph 24 is greatest at $\lambda_1$. In the second state, represented by graph 26, the system is configured such that the filter assembly 16 has a second assay disposed on one of its surfaces 32 that is exterior to the optical assembly 18. The second assay is bound to a target analyte and therefore graph 26 represents a second state of the system with a second set of optical characteristics associated with the laser light. In this example, the analyzer 22 has determined that the optical power illustrated in graph 26 is greatest at $\lambda_2$. In this example, the shift in wavelength from $\lambda_1$ to $\lambda_2$ indicates the presence of the analyte in the second assay.

The laser output optical wavelength and power are extremely sensitive to the various elements of the laser system. The double pass gain of a laser may be approximated with the following mathematical expression:

$$\text{gain}(\lambda) \approx G(\lambda)^2 R_1(\lambda) R_2(\lambda) e^{(-2\alpha(\lambda)L)} \qquad \text{Equation 1}$$

In Equation 1, $\lambda$ is the optical wavelength of the laser output, G is the single pass gain of the optical gain medium, $R_1$ and $R_2$ are reflectance values of the cavity mirrors, alpha is the passive loss and L is the cavity length. Typically, a broadband laser emits power at a wavelength that corresponds to the wavelength at which the laser resonating cavity has the lowest loss. It will be appreciated that an appropriate broadband filter can be designed such that the minimum wavelength dependent loss occurs at the desired lasing frequency. It will also be appreciated that the reflectance properties of the lasing cavity can be used to preferentially select the lasing wavelength. A shift in the wavelength of the reflector alters the resonating cavity by providing maximum gain at a different wavelength. As seen by Equation 1, the correlation between the gain at a certain wavelength and the wavelength of the reflector is linear.

It will be appreciated that in some embodiments, a broadband light source and a filter configured to select predetermined wavelengths can be used instead of a laser light source.

Figure 2:
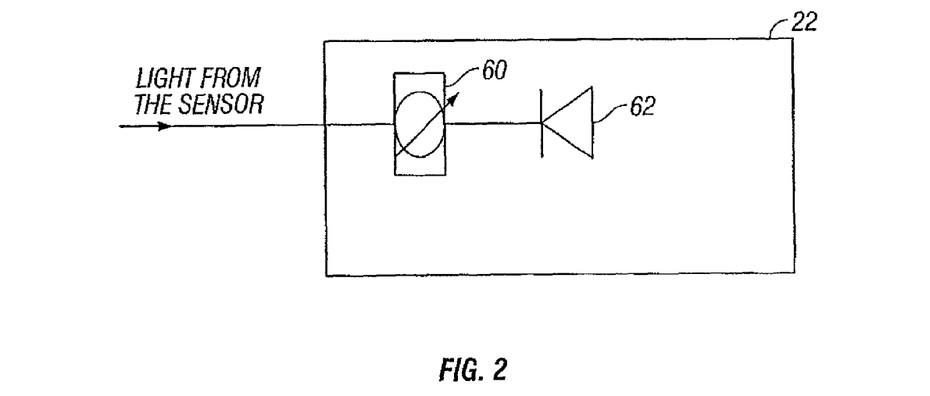
FIG. 2 is a schematic illustrating one embodiment of an analyzer having a tunable filter and a photodiode.

FIG. 2 is a schematic diagram illustrating an alternative embodiment of the analyzer 22, where the analyzer 22 can determine the wavelength of the light exiting optical assembly 18 using an optical filter and sensor. There are a variety of commercially available analyzers 22 that can be employed to determine a shift in wavelength of the light exiting the sensor 16 (FIG. 1). A suitable analyzer 22 to determine a change in wavelength can also be formed using less expensive means. In one embodiment, the analyzer 22 includes a tunable filter 60, positioned to receive light from the optical assembly 18, and a photo diode 62 positioned to receive light from the tunable filter 60. As shown in FIG. 2, to determine if a change has occurred in an assay on the filter assembly 16 (FIG. 1), light propagating from the sensor 34 (FIG. 1) is communicated into the analyzer 22 and enters the tunable filter 60. The pass band of the tunable filter 60 can be controlled, automatically or manually, to scan the optical bandwidth of interest for the light, for example, an optical bandwidth that includes wavelengths $\lambda_1$ and $\lambda_2$ as shown in FIG. 1. The photodiode 62 receives light passing through the tunable filter 60 during the time period that the tunable filter 60 is scanning the optical bandwidth of interest. The output current of the photodiode 62 correlates to the total amount of light that exits the tunable filter 60 at each scanned wavelength. By scanning the entire optical bandwidth of interest with the tunable filter 60 while the tunable filter 60 is receiving light from the optical assembly 18, the maximum measured current output by the photodiode 62 can be identified and correlated to the maximum power and wavelength of the signal exiting the optical assembly 18. Accordingly, a shift in wavelength, for example, from $\lambda_1$ to $\lambda_2$ (FIG. 1) can be identified, which indicates the presence of the analyte in an assay disposed on the filter assembly 16 (FIG. 1).

Figure 3:
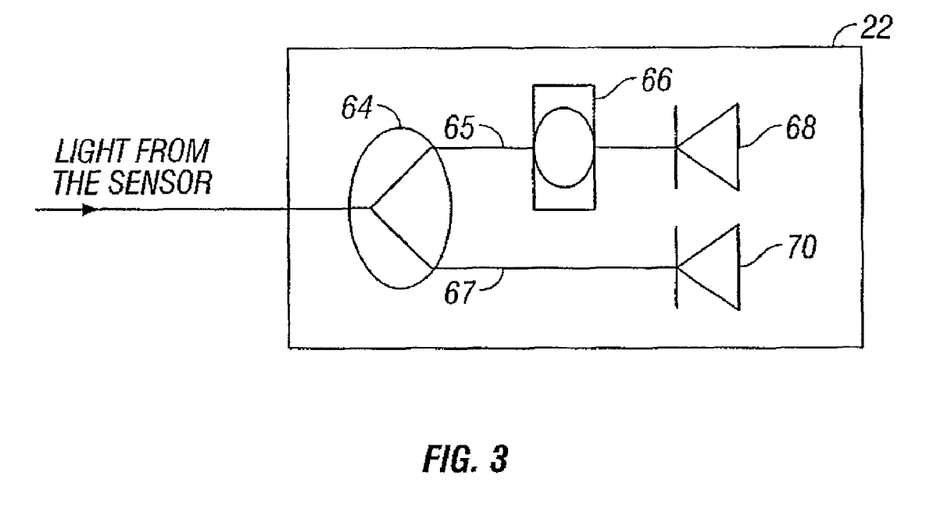
FIG. 3 is a schematic illustrating one embodiment of an analyzer having a filter and two photodiodes.
Figure 4:
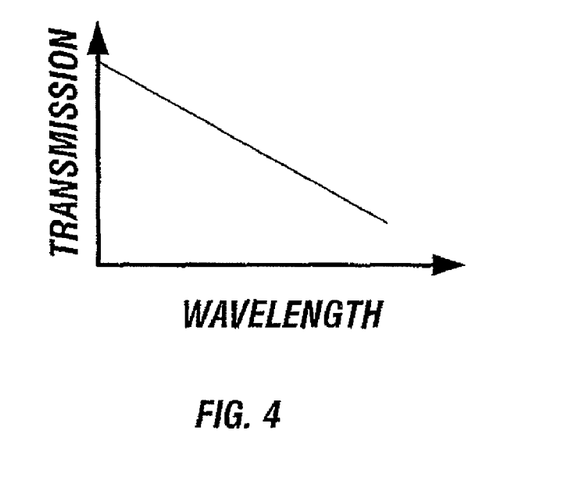
FIG. 4 is a graph illustrating an example of a filter response of the filter shown in FIG. 3.

FIG. 3 illustrates another embodiment of the analyzer 22. As shown in FIG. 3, the analyzer 22 in this embodiment includes an optical splitter 64 positioned to receive light propagating from the sensor 34 (FIG. 1). The analyzer 22 also includes a static filter 66 positioned to receive light from the optical splitter 64, and a first photodiode 68 positioned to receive light from the static filter 66 and a second photodiode 70 positioned to receive light from the optical splitter 64. The static filter 66 has a known spectral response, which can be the filter spectral response shown in FIG. 4. The analyzer 22 is configured so that light from the sensor 34 enters the analyzer 22 and is split by the optical splitter 64 so that it propagates along a first path 65 and a second path 67. Light propagating along the first path 65 passes through the static filter 66 and is received by the first photodiode 68. Light propagating along the second path 67 is received by the second photodiode 70. The output current of the first photodiode 68 and the second photodiode 70 correlate with the signal that each photodiode receives. By comparing the output of the two photodiodes 68, 70 and knowing the spectral response of the static filter 66, one can compute the total power and wavelength of the signal leaving the sensor 34 at any time using the following equations:

$$P = 2Pd_2 \qquad \text{Equation 2}$$

$$\lambda = g(Pd_1/Pd_2) \qquad \text{Equation 3}$$

where P is the power of the signal, $\lambda$ is the wavelength of the signal, $Pd_1$ is the voltage at the first photodiode 68, $Pd_2$ is the voltage at the second photodiode 70, and g( ) is the known response function of the static filter 66. In another embodiment (not shown), the sensor 34 (FIG. 1) has a certain spectral response so that a change in the assay results in a known change in power in the light from the sensor. In such an embodiment, a single photodiode can be configured in the analyzer 22 to receive and monitor the light from the sensor 34 to identify a relevant power change, and the analyzer 22 can determine a change in the assay based on detecting the known change in power.

The embodiment shown in FIG. 1 can also be incorporated into a high throughput system ("HTS") for analyzing numerous assay reaction spots disposed on a filter assembly 16. For example, the filter assembly 16 can be formed by a strip that has up to 50 or more reaction spots disposed on its surface. Numerous strips can be joined together to form a microarray comprising rows and columns of reaction spots. In some embodiments, the high-throughput system can have up to 40,000 spots formed into a microarray on the filter assembly 16. In some embodiments, a high-speed X-Y scanning process can be employed to determine information about the reaction in each of the spots in the microarray, where the filter assembly 16 is stepped in one direction (e.g., X) and the scanning is done in the other direction (e.g., Y).

Figure 5:
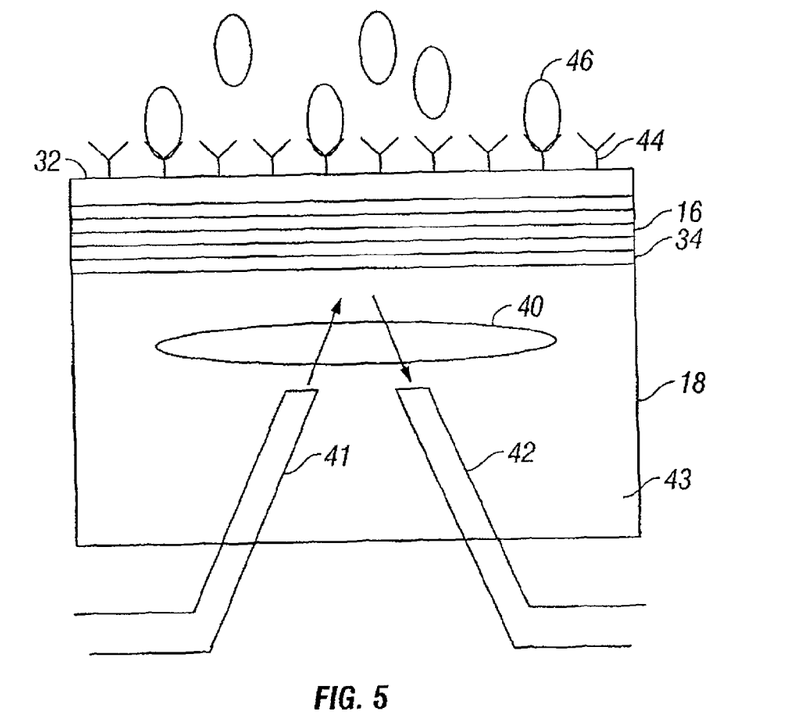
FIG. 5 is a schematic diagram of an optical assembly for use in a bio-sensor system, the assembly configured with a filter assembly having a reflective thin-film stack.
Figure 6:
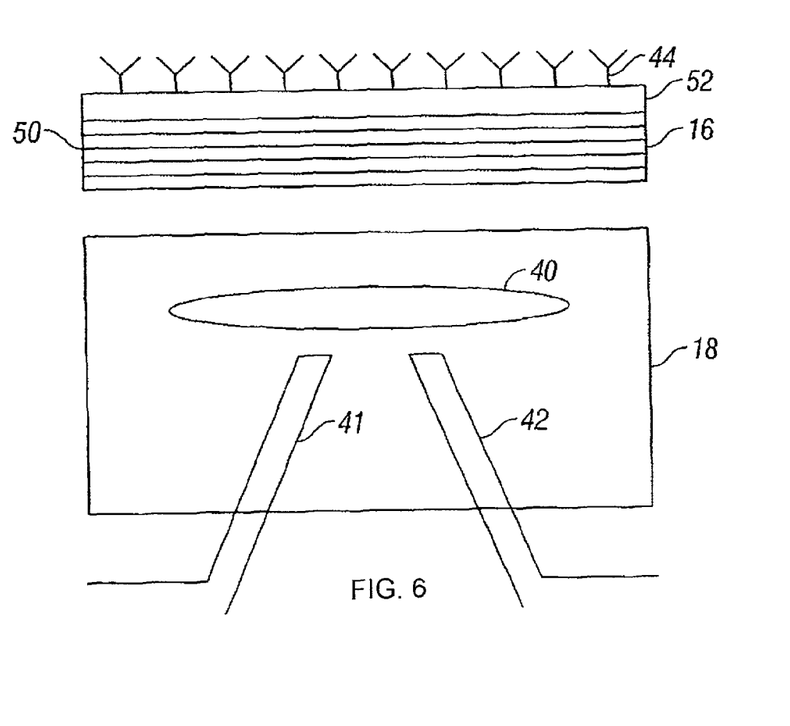
FIG. 6 is a schematic diagram of the optical assembly and filter assembly shown in FIG. 5 with the filter assembly removed from the optical assembly.

FIG. 5 illustrates a more detailed view of the embodiment of the optical assembly 18 and filter assembly 16 of FIG. 1. Here, the optical assembly 18 is illustrated with the filter assembly 16 secured thereto. As shown in FIG. 6, the filter assembly is removable from the optical assembly. In some embodiments, the filter assembly 16 or parts of the filter assembly 16 can be made to be disposable. In this embodiment, the filter assembly 16 is configured as a reflection filter. Light from the gain medium 14 (FIG. 1) enters the optical assembly 18 through an entrance fiber ferrule 41. A lens assembly 40 comprising one or more optical elements is positioned between the entrance fiber ferrule 41 and the filter assembly 16 so that it collimates light emitted from the entrance fiber ferrule 41 and provides the collimated light to the filter assembly 16. In some embodiments, the lens assembly 40 comprises one or more lenses to collimate the light. The lens assembly 40 also collimates the light reflected by the filter assembly 16 such that the reflected light propagates into exit fiber ferrule 42. A portion of the light that enters the exit fiber ferrule 42 is provided to the analyzer 22 (FIG. 1) and a portion is provided to the optical fiber 28 (FIG. 1) which is configured to circulate the light through the gain medium 14 (FIG. 1).

A biochemical reaction site can be formed by depositing an assay 44 on the surface 32 of the filter assembly 16. The assay 44 is disposed outside the cavity in the optical assembly 18, e.g., on an exterior surface of the filter assembly 16 when the filter assembly 16 is secured to the optical assembly 18. While one surface 32 is exposed to a bio-molecular reaction, the opposite surface is coupled optically to the fiber laser ensemble, forming a part of the lasing cavity.

It will be appreciated that the assay 44 is configured such that the reaction of the assay 44 with a target analyte 46 results in a physical change of the assay that results in a change of one or more optical properties of the filter assembly 16. Depending on the particular configuration of an embodiment, reagents and samples can be exposed to the assay 44 in numerous ways. For example, one of the numerous microfluidic flow systems can be used to control the exposure of the assay 44 to reagents and samples. Microfluidic flow systems are available commercially and can be adapted for this application. Also, micropipettes can be used to provide samples and reagents to the assay 44. In some embodiments, the micropipettes are used manually, in other embodiments the micropipettes are incorporated in a system to apply the samples and reagents to the assay 44 automatically. In a further embodiment, the assay 44 can be exposed to the samples and reagents by dip-coating, for example, dipping the assay 44 in the desired sample or reagent.

Changes to the assay 44, e.g., a change of thickness of the bio-molecular layer of the assay, a change in the refractive index, or both, can result in a change (e.g., a distortion) of the signal reflected by the filter assembly 16 inside the optical assembly 18. For example, when the assay 44 is exposed to a target analyte 46, the assay 44 binds to the target analyte 46 and the assay 44 becomes thicker and/or the assay 44 changes the refractive index at the surface 32 that it is disposed upon. The effect of this change is significantly amplified within the lasing cavity and results in a change in one or more characteristics of the laser light. For example, this change can result in a shift in the resonating wavelength of the laser. Knowing the characteristics of the laser light produced in the resonating cavity before the biochemical reaction takes place in the assay 44, a detected change in a characteristic of the laser light can be correlated to a biomolecular event in the assay 44.

The optical assembly 18 can be configured to receive and hold the filter assembly 16 so that a biochemical reaction in the assay 44 can be detected and analyzed. In some embodiments, the filter assembly 16 can be optically coupled to the entrance fiber ferrule 41 and the exit fiber ferrule 42. In some embodiments, the filter assembly 16 can be incorporated in a structure that is optically coupled to the optical assembly 18. The filter assembly 16 can be coupled to the optical assembly 18 in a variety of ways to ensure the filter assembly 16 is positioned in the path of the optical beam emitted from the entrance fiber ferrule 41. For example, in one embodiment, a tongue and groove configuration can be used where the filter assembly 16 is mechanically aligned to the optical assembly 18. In another embodiment, a pin assembly can couple the filter assembly 16 to the optical assembly 18. In some embodiments, the filter assembly 16 is first automatically aligned with the optical assembly 18 using fiducials on the filter assembly 16 that are read by a system (not shown) that provides feedback as to the alignment of the filter assembly 16. In one such embodiment, the feedback system includes using an optical feedback system. In some embodiments, the feedback system includes using an electrical or electronic feedback system. In some embodiments, the feedback system includes a combination of electrical and optical systems. Once the filter assembly 16 is aligned with the optical assembly 18, the filter assembly 16 can be coupled to the optical assembly 18 using various mechanical coupling means, including, for example, a micro gripper, or air suction (e.g., a vacuum).

FIG. 6 illustrates an embodiment where the filter assembly 16 can be removed from the optical assembly 18 so that another filter assembly 16 can be received in its place. The optical assembly 18 can receive a variety of filter assemblies which each can be configured with a particular filter, e.g., one of the filters described above.

In one embodiment, the filter assembly 16 includes a thin-film reflectance filter 50 having one or more layers and a overlay or sensing layer 52. In one embodiment, the thin film filter 50 includes 10 alternating layers of SiO and $SiO_2$. The filter assembly 16 has reflection characteristics of a raised cosine 100 nm or less in bandwidth and 100% deep such that a change in the refractive index of the overlay region 52 results in a linear shift in the center wavelength of the filter. In one embodiment, the filter assembly 16 is configured to have the greatest possible shift in center wavelength (CW) when the overlay layer 52 has a thickness of about 1 nm and a refractive index of about 1.38. The characteristics of one embodiment of the filter assembly 16 are shown in Table 1 (below):

| Parameter | Value | Comment |
|---|---|---|
| Filter Bandwidth (BW) | <100 nm | Operates in the L band. |
| Start Wavelength | 1540 nm | |
| Stop Wavelength | 1640 nm | |
| Center Wavelength (CW) | 1580 nm | Defined as the wavelength corresponding to maximum reflectance. |
| Filter Depth (D) | >40 nm | The change in reflectance from CW to CW + BW/2 |
| Sensitivity (S) | >0.1 nm/nm | The change in CW as a function of thickness of overlay layer where the overlay layer has a refractive index (RI) of 1.38 |
| Optical Power | 500 mW | Maximum optical power incident on filter |
| Out of bandwidth performance | None | Optical characteristics outside the bandwidth are not specified. |
| Temperature Dependence | <0.1 pm/° C. | Defined as the shift in center wavelength of the filter as a function temperature. |
| Filter Substrate | None | No constraints on the choice of filter substrate |

Table 1

Using the terminology defined in Table 1, a figure of merit (FOM) is defined for the filter assembly as:

$$FOM = \frac{D * S}{BW} \qquad \text{Equation 4}$$

where D is the filter depth, defined as the change in reflectance from center wavelength ("CW") to CW+BW/2, BW is the filter bandwidth, and S is the sensitivity. The ideal filter could have a peak reflectivity of unity, minimum reflectivity of zero (D=1), a narrow optical bandwidth and a high sensitivity. In practice, these parameters can be selected based on the constraints of a particular implementation. In one embodiment, the objective of the design is to maximize the FOM. In one embodiment, the filter assembly has a filter bandwidth (BW) of less than about 100 nm, a peak reflectivity of about 40% and a rate of change of around 0.1 nm.

Figure 7:
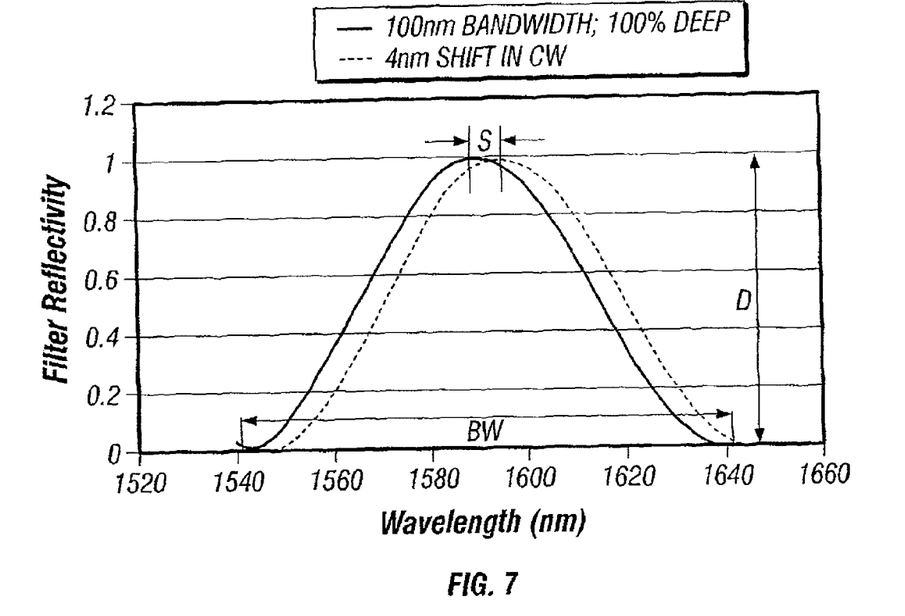
FIG. 7 is a graphical diagram illustrating the definition of filter performance parameters of the filter assembly shown in FIG. 5.

The parameters Center Wavelength (CW), Filter Depth (D), and sensitivity (S) are graphically illustrated as an example of one embodiment in FIG. 7.

Figure 8:
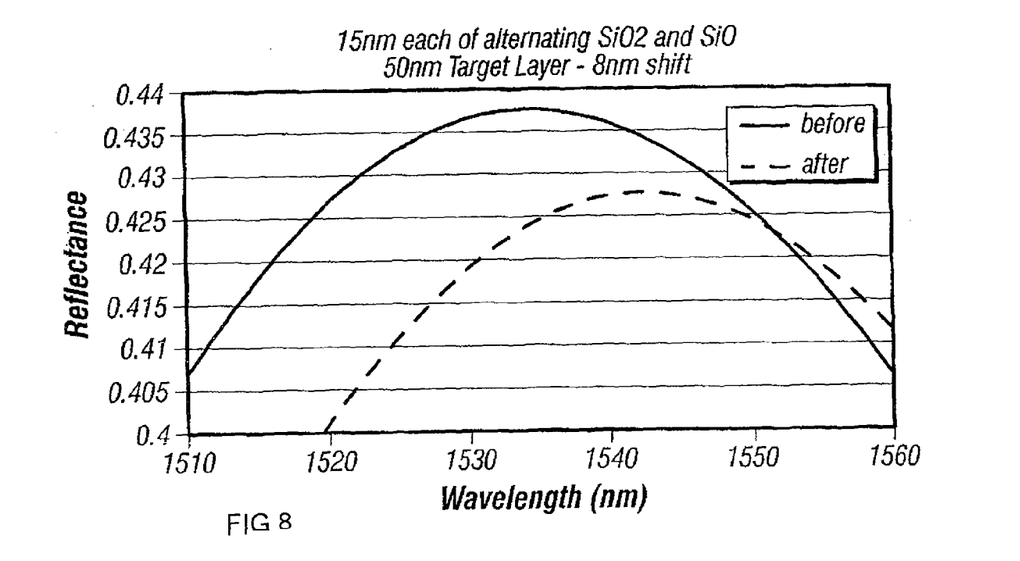
FIG. 8 is a graphical diagram of reflectance as a function of wavelength for one embodiment of the filter assembly shown in FIG. 5.

FIG. 8 illustrates the relationship between wavelength and reflectance of one embodiment of a filter assembly having a sensitivity (S) of 0.1, a filter bandwidth (BW) of 100 nm, and a filter depth of 30% from its peak reflectivity.

In some embodiments, the filter assembly can be configured with wavelength characteristics using multiple thin film coatings of $SiO_2$ and $Al_2O_3$ forming a thin-film stack with Bragg properties. A large variety of organic and inorganic material may be used to obtain the desirable reflectance characteristics. The Bragg wavelength is given by Equation 5:

$$\lambda_B = 2\Lambda n_r \quad \text{Equation 5}$$

where $\Lambda$ is the period of the perturbation and $n_r$ is the refractive index of the material. Note that in the cases of fixed thickness and periodicity, the Bragg wavelength depends linearly on the refractive index of the material.

In some embodiments, the filter assembly consists of a thin film stack, having alternating layers of high and low refractive index material. The equation for such a thin film stack is adapted from "Optical Filter Design and Analysis—A signal Processing Approach" by C. K. Madsen and J. H. Zhao—Chapter 5, for example, equation 68, that describes a characteristic matrix of a thin film stack. For a stack of 'm' layers, the electric ($E_m$) and magnetic ($Z^*H_m$) fields can be described by Equation 6:

$$\begin{bmatrix} E_m \\ ZH_m \end{bmatrix} = \begin{bmatrix} 1 & 1 \\ n_m & -n_m \end{bmatrix} \begin{bmatrix} E_m^+ \\ E_m^- \end{bmatrix} \quad \text{Equation 6}$$

where $E^+$ and $E^-$ are the appropriate polarizations, and $n_m$ is the refractive index of the $m^{th}$ layer. The $m^{th}$ layer, the electric and magnetic fields are given by Equation 7:

$$\begin{bmatrix} E_m \\ ZH_m \end{bmatrix} = \begin{bmatrix} \cos\phi_{m-1} & \dfrac{j\sin\phi_{m-1}}{n_{m-1}} \\ jn_{m-1}\sin\phi_{m-1} & \cos\phi_{m-1} \end{bmatrix} \begin{bmatrix} E_{m-1} \\ ZH_{m-1} \end{bmatrix} \quad \text{Equation 7}$$

$$= M_{m-1} \begin{bmatrix} E_{m-1} \\ ZH_{m-1} \end{bmatrix}$$

$$\text{where } \phi_m = \left(\frac{2\pi}{\lambda}\right) n_m d_m$$

for light that is incident normal to the thin film stack and $n_m$ and $d_m$ are the refractive index and thickness of the $m^{th}$ layer respectively. $M_{m-1}$ is the characteristic matrix for the m–1 layers—determined by successive application of Equation 7.

The electric field of a thin film stack is described by combining Equations 6 and 7, shown in Equation 8:

$$\begin{bmatrix} E_m^+ \\ E_m^- \end{bmatrix} = \begin{bmatrix} 1 & 1 \\ n_m & -n_m \end{bmatrix}^{-1} M_m \begin{bmatrix} 1 & 1 \\ n_0 & -n_0 \end{bmatrix} \begin{bmatrix} E_0^+ \\ E_0^- \end{bmatrix} \quad \text{Equation 8}$$

$$= \begin{bmatrix} Q_{11} & Q_{12} \\ Q_{21} & Q_{22} \end{bmatrix} \begin{bmatrix} E_0^+ \\ E_0^- \end{bmatrix}$$

Using this equation, the transmission (T) and reflectance (R) is given by Equation 9:

$$T(\lambda) = \frac{1}{Q_{11}(\lambda)} \text{ and } R(\lambda) = \frac{Q_{21}(\lambda)}{Q_{11}(\lambda)} \quad \text{Equation 9}$$

Depending on a particular embodiment, a user can specify the thickness, refractive index and the number of layers for the high and low index material that is used to make the thin film stack. The user can also specify the thickness and refractive index of the bio layer in the 'before' and 'after' case. In some embodiments, the desired filter characteristics may also be obtained with a Bragg grating or a Fabrey-Perot etalon filter.

Figure 9:
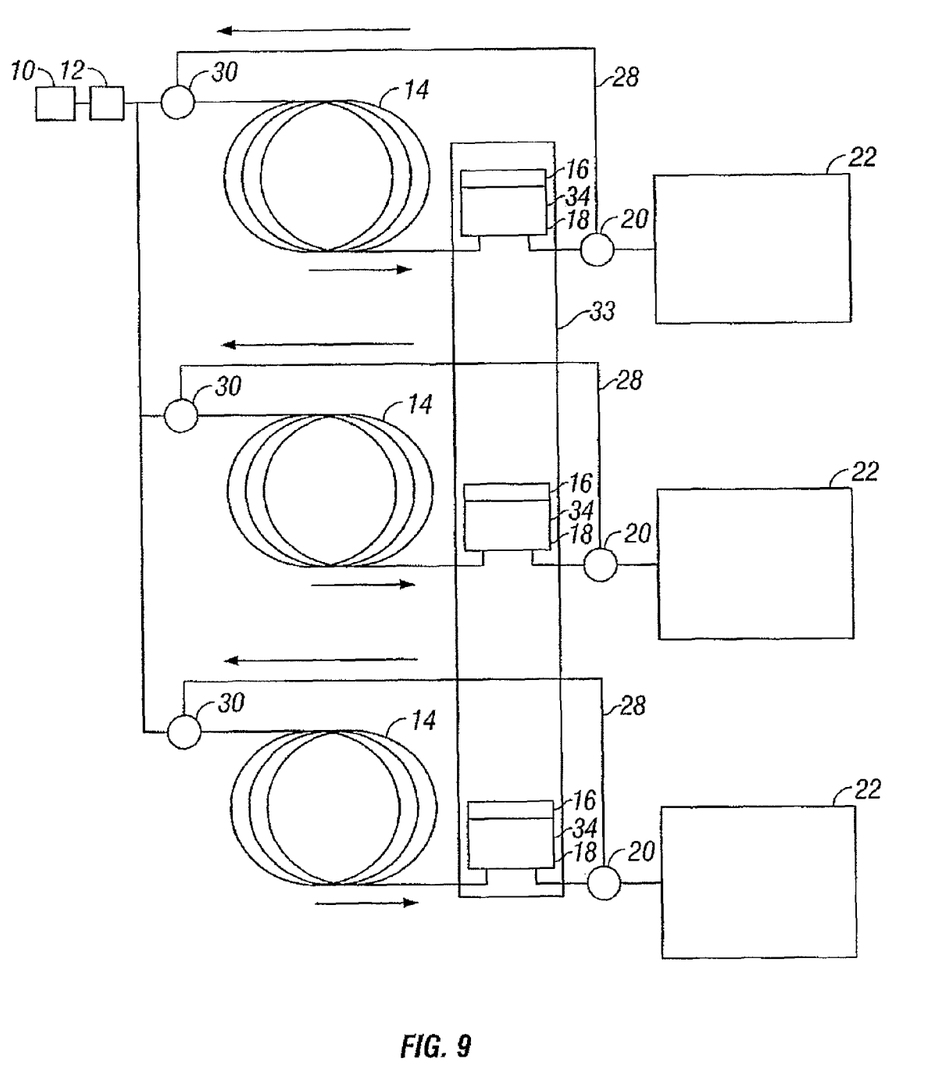
FIG. 9 is a diagram illustrating one embodiment of a bio-sensor system having multiple sensor sites for detecting an analyte without the aid of secondary identifier tags.

FIG. 9 illustrates an embodiment of a system that includes multiple resonating cavities and an array 33 of sensor sites 34 (e.g., biochemical reaction sites), each sensor site 34 including an optical assembly 18 and a filter assembly 16. In some embodiments, the sensor sites 34 can be arranged on a single fixture which can be configured such that the entire fixture is disposable or reusable. Configurations incorporating multiple sensor sites allow the arrangement of multiple biochemical interactions on the sensor sites 34 which can be independently monitored to determine the results of reactions in the assays.

It will be appreciated that many embodiments of the array 33 are considered for testing analytes with multiple sensor sites. For example, in one embodiment, the multiple sensor sites in the array 33 can contain the same assay designed to detect the same analyte. In another embodiment, the multiple sensor sites in the array 33 can contain different assays designed to detect different analytes. In one embodiment, the sites in the array 33 include a set of two or more similar assays where the assays include differences designed to detect one or more particular characteristics of an analyte present in a sample. For example, a set of assays can be designed to detect the concentration of an analyte present in the samples. In some embodiments, a particular characteristic can be detected by analyzing which assay(s) in the set reacted, where in other embodiments the analysis of the reactions that occurred in two or more assays in the set of assays yields information on a particular characteristic of the analyte, or on a unique combination of the analytes present.

Various configurations of the sites in the array 33 can be used depending on the implementation desired. In one embodiment the sites in the array 33 can be used to detect an analyte from a single sample. In another embodiment, the sites in the array 33 can be used to detect an analyte from a plurality of samples. In some embodiments, the sites in the array 33 can be designed so that the results from two or more sites in the array 33 can be used to detect different combinations of analytes in a given sample, which can convey information regarding the source, content, health, and/or quality of the sample. In addition, multiple sensor sites can be used to determine information of multiple analytes in a sample, where the different combination of analytes present in a given sample convey a message regarding the source, content, health or quality of the subject from which the sample was extracted.

Three resonating cavities are shown in the embodiment of FIG. 9, but it will be appreciated that embodiments can include two resonating cavities or more than three resonating cavities. A single optical pump 10 for generating pump radiation can be shared among the resonating cavities, as shown. In some embodiments, multiple optical pumps can be used. FIG. 9 illustrates representations of three analyzers 22 that receive and analyze the light from the sensor sites 34. In practice, a single analyzer can be configured to receive the light from multiple sensor sites 34 (e.g., in a sequence using an optical switch) and analyze one or more characteristics of each. In some embodiments, a single wavelength detecting analyzer 22 is shared by all the resonating cavities using an optical MUX assembly. In some embodiments, the analyzer 22 can determine a characteristic of the light using a photodiode and a tunable narrow band filter, as described above in reference to FIGS. 2-4. In some embodiments, the analyzer 22, or another system that receives data from the analyzer 22, can generate a report describing the results of the analyte testing. The report can include the status of the assay, for example, whether binding has occurred, and/or how much binding has occurred. This report is typically provided to the user. In some embodiments, the report is communicated to a third party, for example a point-of-care service, via a wired or wireless communications means, for example, a modem, facsimile machine, or the internet.

In some embodiments, the analyzer 22 includes a system having a signal processing unit (not shown) that monitors each of the biochemical reaction sites, and interprets and reports on the reactions occurring at one or more sensor sites 34. Signal processing analysis includes using the multiple calibration information, real time information of the environmental conditions and effects on the system and the signal from the sensor to determine the binding status of the assay 44. In some embodiments, the signal processing unit interprets results from multiple biochemical sites and provides the user information of the biochemical reactions (e.g., the kinetics) occurring at each site. One advantage of the embodiments described herein is that process variations during manufacturing of the pieces used in the instrument can be factored into the calibration of the system. The signal processing can include using multiple calibration information, real time information on the environmental effects on the system, and the signal from the sensor 34 to determine information of the binding of the assay.

In some embodiments, the filter is designed to correspond to or match the non-linear wavelength dependent gain profile of the optical gain medium within the laser resonant cavity. This can be applicable, for example, to embodiments illustrated in FIGS. 5 and 6 where an optical gain medium in a resonant cavity is coupled, using optical fibers 41, 42, to an interchangeable sensor site 34 that includes a filter assembly 18 and an assay 44 disposed on the overlay layer 52. The filter assembly 16 can be configured to have a reflectivity profile that determines, in part, lasing power and wavelength of the laser analysis system.

Figure 10:
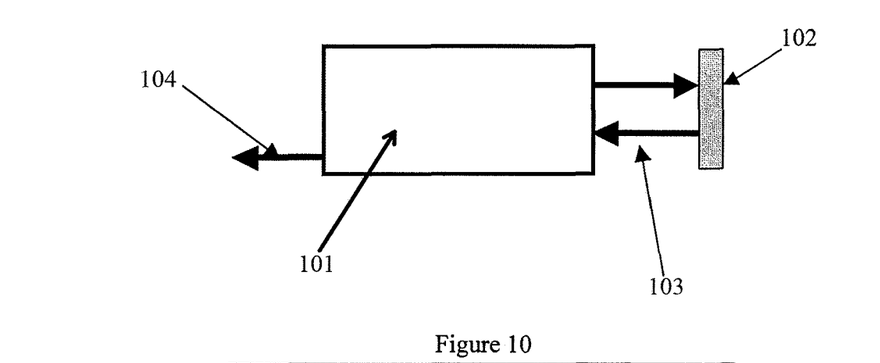
FIG. 10 is a schematic that illustrates an embodiment where a gain medium in a laser resonating cavity is coupled to a filter assembly.

FIG. 10 is a schematic that illustrates an embodiment where a gain medium 101 in a laser resonating cavity is coupled to a removably attachable filter assembly 102 using optical coupling means 103, for example, micro-coupling optics. At least a portion of the light propagating in the laser resonating cavity is incident on the filter assembly 102. One or more characteristics of the propagating light (e.g., wavelength, frequency, or power) is affected by the reflectivity profile of the filter assembly 102. Changes to the one or more characteristics of the light can be monitored by evaluation of light 104 transmitted to an analysis system (not shown) to determine information about a reaction in an assay on the filter assembly 102.

Figure 11:
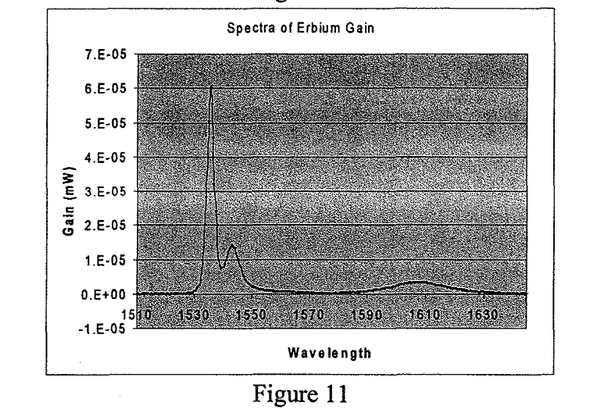
FIG. 11 is a graphical diagram illustrating a wavelength dependent non-linear gain profile of an erbium based gain medium.

FIG. 11 is a graph that illustrates a wavelength dependent non-linear gain profile of an erbium-based gain medium that may be used in some embodiments of the invention. The gain (y-axis) is shown as a function of wavelength (x-axis). The highest gain occurs at a wavelength between about 1530 nanometers and about 1540 nanometers. Other optical gain materials, including but not limited to ytterbium, neodymium, erbium/ytterbium, can also be used, each yielding a specific gain profile.

Figure 12:
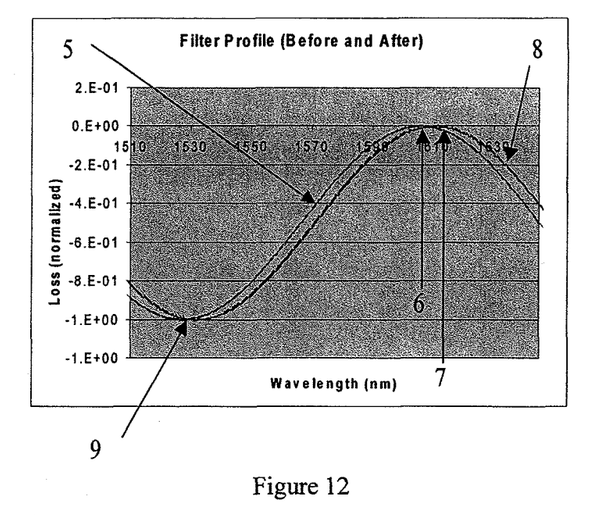
FIG. 12 is a graphical diagram illustrating a filter profile that is characterized by a raised cosine characteristic selected such that its maximum loss coincides with the region where the gain medium has the highest gain.

FIG. 12 is a graph that illustrates an example of (normalized) loss verses wavelength for a particular filter assembly, referred to herein a filter assembly profile. The filter assembly is configured such that the profile has a raised cosine characteristic having its maximum loss 109 about coincident with the region where the gain medium illustrated in FIG. 11 has the highest gain. The filter assembly can be configured such that its loss profile 105 before a reaction occurs matches the gain profile of the lasing medium so that it causes a resonant lasing cavity to have a maximum laser output in the area indicated by 106 that corresponds to a spectrally broad and uniform gain region of the gain medium shown in FIG. 11 at about 1610 nanometers. The filter is further designed such that a reaction to the assay deposited on the first surface placed outside the laser resonating cavity, causes the filter loss profile to shift in wavelength indicated at 107 such that its minimal loss center wavelength is shifted to loss profile 108 to another region that the laser gain material provides gain. This example shows a linear shift in filter loss profile such that the center wavelength of the filter bandwidth towards longer wavelengths (e.g., red) resulting from a change in the assay on the first surface of the filter. In other embodiments, numerous filter assembly profiles are possible where the shift in filter loss profile may be towards shorter wavelengths (e.g., blue), including changes in the overall filter characteristics.

Figure 13:
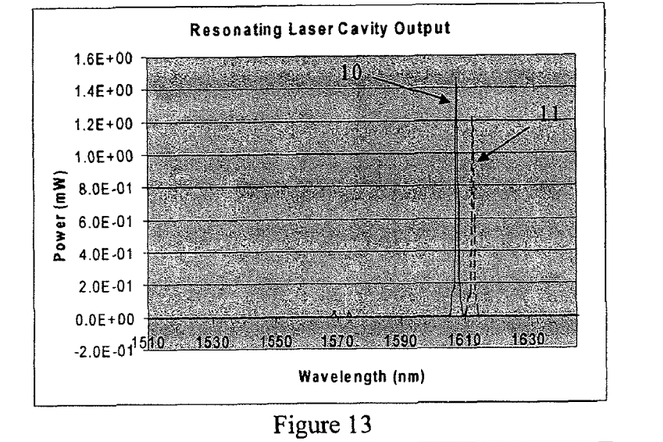
FIG. 13 is a graph depicting Power (y-axis) as a function of Wavelength (x-axis) that illustrates a power shift caused by a reaction in an assay.

FIG. 13 shows an output of a laser resonating cavity caused by the design of the removable filter assembly. The filter choice nominally causes the laser resonating cavity to have a laser output 110 of about 1.5 mW at a wavelength of about 1608 nm. The shift in loss profile of the removable filter assembly resulting from reactions at the assay layer on its first (outer) surface (e.g., loss profile 108 in FIG. 12) causes the light propagating in the entire resonating cavity to have a shift in laser output 111 to about 1613 nm. Because of the non-linear gain profile of the gain medium, a change in power is anticipated at the new resonating laser output wavelength. This shift in laser resonating output can be monitored and used to gather information on the reaction of one or more assays disposed on the filter assembly.

Figure 14:
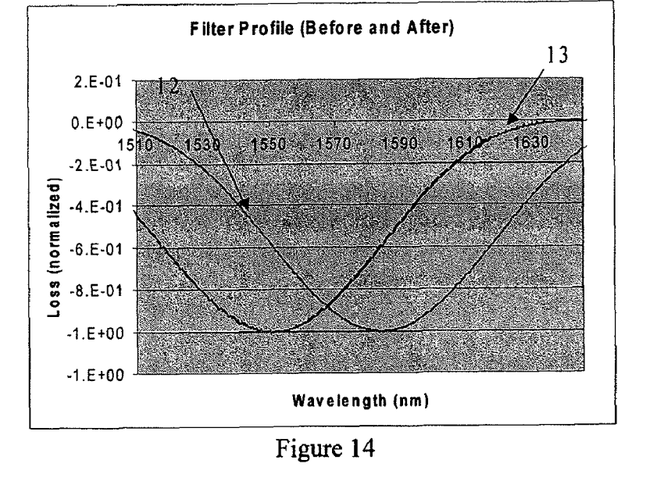
FIG. 14 is a graphical diagram illustrating a filter profile by showing the filter loss (normalized) as a function of wavelength before and after a reaction occurred in an assay on the filter.

FIG. 14 illustrates filter loss profiles in a graph of filter loss (normalized) as a function of wavelength before (profile 112) and after (profile 113) a reaction occurred in an assay on the filter assembly. A filter assembly can be designed such that in operation it has a filter loss profile 112 that exhibits loss throughout the gain band of a gain medium in a resonating cavity, for example, the erbium gain medium profile shown in FIG. 11 so that no resonance occurs in a first state. The filter assembly can be configured such that a reaction in an assay deposited on the first surface of the filter assembly would cause the filter loss profile to shift such that a part of the gain material is no longer subject to the filter loss profile so that light propagating in the gain medium begins to resonate and provide a laser output. In other words, the filter is designed nominally to keep the laser output to operate below a resonating threshold and, accordingly, provide no lased output. The filter assembly will cause the light propagating in the gain medium to cross a lasing threshold only when a certain reaction occurs in the assay deposited on the filter assembly. A reverse configuration is similarly possible where the removable filter is designed to cause the laser resonating cavity to lase under nominally conditions, but stop lasing when the assay deposited on the first surface of the filter reacts to cause the reflectance characteristics of the filter assembly to shift to a position of the loss profile where the gain bandwidth of the optical gain medium is sufficiently suppressed.

Figure 15:
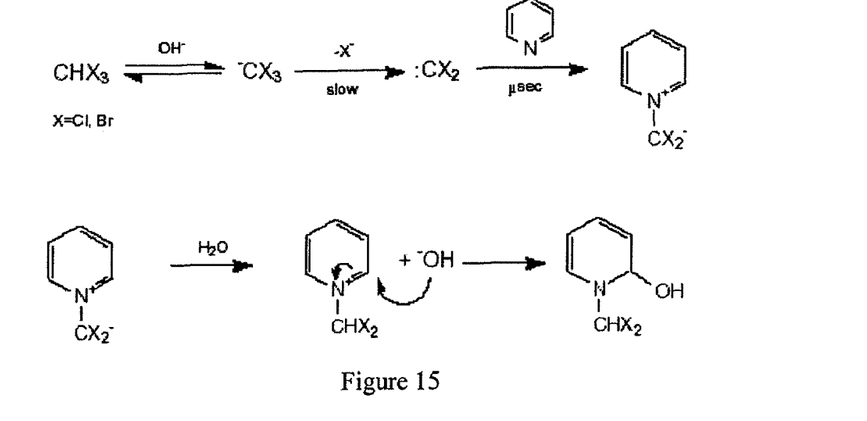
FIG. 15 illustrates the solid-phase THM detection process of a removable filter.

FIG. 15 illustrates the solid-phase THM detection process of a removable filter. The assay deposited on the first surface of the filter can consist of a chemical layer that reacts in the presence of a particularly targeted analyte. For instance, as an illustrative example, an overlay surface of a filter assembly is deposited with a pyridine-based conjugated polymers that forms an active assay. Trihalomethanes, a known carcinogen in water supplies produced by bleach-based compounds, are known to participate in Fujiwara reaction that involves the reaction of pyridine, hydroxide, with halogenated hydrocarbons to give products that absorb strongly in the visible or long ultraviolet regions (modified optical density). The product in such reactions is (colorless) glutaconaldehyde, obtained by N-alkylation of pyridine followed by complete ring hydrolysis. However, depending on the analyte and on the specific reaction conditions, a number of Schiff base derivatives of glutaconaldehyde may form as reaction intermediates, and more than one molecule of glutaconaldehye may be obtained per molecule of analyte. Specifically, FIG. 15 describes the solid-phase toxic heavy metal ("THM") detection process on a removable filter. In the presence of THMs, the pyridine inside the polymer is rapidly consumed (e.g., having a reaction time of microseconds) into metastable intermediary compounds via numerous pathways. Within one to two minutes, depending on the type and concentration of THMs, a reaction region will first change in optical density followed by the localized consumption (denaturing) of the polymer. Both consequences, the change in optical density as well as the consumption of the polymer, can be continuously monitored, and recorded, by the determining changes that occur in one or more characteristics in the light output of the laser resonating cavity.

Depending on the particular configuration of an embodiment, custom software and electronics can monitor the light from the sensor site 34 or a signal derived from the light (e.g., an electrical signal) and report changes in the assay. The system can address one or more of a number of factors to report on the status of biochemical interactions at the sensor, including, for example, system calibration including variations in quality of the assay, instrument and sensor, environmental components (e.g., temperature and pH), long term changes in the system components of the assay (e.g., laser source and assay lifetime), and the relative positioning of the filter assembly 16 with the optical assembly 18 can be sensed and the sensor signal compensated accordingly. In an embodiment that includes an array of sensors 34, for example as shown in FIG. 9, the status of one sensor can be reported in conjunction with the status of other sensors in the array. The signals from the array of sensors can be processed and analyzed in reference to each other, where appropriate. Software to report the status of biochemical interactions may include graphing tools for immediate viewing, wireless reporting of results to a remote site and other such schemes.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. As will be recognized, the present invention may be embodied within a form that does not provide all of the features and benefits set forth herein, as some features may be used or practiced separately from others. The scope of the invention is indicated by the appended claims rather than by the foregoing description. All changes which come within the meaning and range of equivalency of the claims are to be embraced within their scope.

What is claimed is:

1. A device, comprising:
    a filter assembly and an optical assembly, said filter assembly configured to be removably attachable to said optical assembly, said optical assembly and said filter assembly each forming a portion of a laser system laser resonating cavity that includes a gain medium when said filter assembly is attached to said optical assembly, wherein said optical assembly positions the filter assembly to reflect light propagating through the laser resonating cavity when said filter assembly is attached to the optical assembly, said filter assembly comprising an optical structure including
        a first surface having disposed thereon an array of at least one site, each site containing an assay; and
        a second surface configured such that said second surface is disposed within the laser resonating cavity and forms a portion of said laser resonating cavity when said filter assembly is attached to said optical assembly,
    wherein said optical structure is configured to optically interact with said assay to change one or more characteristics of light propagating through said laser resonating cavity and reflecting from said filter assembly based on a reaction that occurs in an assay on said first surface.

2. The device of claim 1, wherein said optical structure comprises at least one partially reflective film layer and an overlay layer, wherein said overlay layer is disposed between said at least one partially reflective film layer and said array, and wherein a portion of said overlay layer comprises said first surface.

3. The device of claim 2, wherein said overlay layer has a thickness of about 1 nanometer and a refractive index of about 1.38.

4. The device of claim 2, wherein a portion of one of said at least one partially reflective film layer comprises said second surface.

5. The device of claim 1, wherein a bandwidth of said optical structure is less than about 100 nanometers.

6. The device of claim 5, where the maximum reflectance of said optical structure is at the center of the bandwidth.

7. The device of claim 5, where the minimum reflectance of said optical structure is at the center of the bandwidth.

8. The device of claim 1, wherein said optical structure has a range of reflectivity over a range of wavelengths, and wherein the reflectivity of said optical structure is lower at a wavelength at an end of said range of wavelengths than at the center of said range of wavelengths.

9. The device of claim 1, wherein said optical structure is configured to have a reflectance profile of a cosine function.

10. The device of claim 1, wherein said one or more characteristics of the light comprises wavelength.

11. The device of claim 1, wherein said first surface comprises a chemically active layer that disintegrates in the presence of chemical or biological agents.

12. The device of claim 1, wherein said array comprises two or more sites containing an assay, and at least two sites contain different assays designed to detect the same analyte.

13. The device of claim 1, wherein said array comprises two or more sites containing an assay, and at least two sites contain the same assay designed to detect the same analyte.

14. The device of claim 1, wherein said array comprises a plurality of sites containing different assays each designed to detect a different analyte.

15. The device of claim 1, wherein said array comprise two or more sites that contain the same assay with varying concentrations designed to detect the concentration of an analyte in a sample.

16. The device of claim 1, wherein said array of one or more sites contain the same assay with varying concentrations designed to detect the concentration of an analyte in a sample.

17. The device of claim 1, wherein said array comprises a microarray of reaction spots which can be analyzed when a portion of said optical structure containing said microarray is disposed to form part of the laser resonating cavity.

18. A filter assembly removably connectable to an optical assembly which forms a portion of a laser resonating cavity of a laser system, the laser resonating cavity having a gain medium, the filter assembly forming a portion of the laser resonating cavity when the filter assembly is attached to the optical assembly and positioned such that light propagating in the laser resonating cavity is incident on the filter assembly, the filter assembly comprising:
   an array comprising at least one site having as assay; and
   an optical structure comprising
      an overlay layer comprising a first surface of the optical structure and including a first surface and a second surface, the first surface having the array disposed thereon, and
      at least one partially reflective film layer comprising a second surface of the optical structure, said at least one partially reflective film layer disposed such that said overlay layer is between said array and said at least one partially reflective film layer,
   wherein the filter assembly is configured such that a reaction that occurs in the assay changes the refractive index of the optical structure thereby changing an optical characteristic of light propagating in the laser resonating cavity and incident on the filter assembly.

19. The filter assembly of claim 18, wherein said overlay layer has a thickness of about 1 nanometer and a refractive index of about 1.38.

20. The filter assembly of claim 18, wherein said array comprises two or more sites each containing an assay, and at least two sites of the array contain different assays designed to detect the same analyte.

21. The filter assembly of claim 18, wherein said array comprises two or more sites containing an assay, and at least two sites contain the same assay designed to detect the same analyte.

22. The filter assembly of claim 18, wherein said array comprises a plurality of sites containing different assays each designed to detect a different analyte.

* * * * *